United States Patent [19]

Hashizume et al.

[11] 3,969,024

[45] July 13, 1976

[54] SIGNAL SEPARATION SYSTEM USED FOR AN AUTOMATED CLASSIFICATION OF WHITE BLOOD CELLS

[75] Inventors: Akihide Hashizume, Kokubunji; Hideki Kohno, Tokyo; Shinji Yamamoto, Hachioji, all of Japan

[73] Assignee: Hitachi, Ltd., Japan

[22] Filed: Aug. 13, 1975

[21] Appl. No.: 604,185

[30] Foreign Application Priority Data

Aug. 14, 1974  Japan.............................. 49-92329

[52] U.S. Cl................................. 356/39; 356/82; 356/201
[51] Int. Cl.²......................................... G01N 33/16
[58] Field of Search.................... 356/36, 39, 81–82; 128/28; 235/151.3, 151.35

[56] References Cited
UNITED STATES PATENTS
3,851,156   11/1974   Green................................ 356/39

*Primary Examiner*—John K. Corbin
*Assistant Examiner*—Wm. H. Punter
*Attorney, Agent, or Firm*—Craig & Antonelli

[57] ABSTRACT

A signal separation system is used to discriminate cytoplasm of white blood cells from a sample of white blood. The signal separation system includes a light source generating light passed through a blood sample, a light separator for separating green and blue light beams from the light passed through the sample, first and second photoelectric converters for changing the green and the blue light beams to first and second electric signals, a signal treatment circuit which converts the first and the second electric signals to binary signals with respect to certain threshold levels and then forms a separation signal from the binary signals, and the gate circuit which separates the signal component of the white blood cells from the sample with the function of the separation signal.

15 Claims, 8 Drawing Figures

SIGNAL SEPARATION SYSTEM USED FOR AN AUTOMATED CLASSIFICATION OF WHITE BLOOD CELLS

BACKGROUND OF THE INVENTION

Field of the Invention

This invention relates generally to a pattern recognition system and, more particularly, to a signal separation system to discriminate cytoplasms of white blood cells from a sample of whole blood in an automated classification of the white blood cells.

It is well known that an examination as to the classification of the white blood cells in whole blood and the existence of abnormal white blood cells therein is effectively used in the diagnosis of humans. The examination due to the classification of the white blood cells is therefore important in clinical examinations. In order to achieve an automatic examination for the classification of white blood cells, various techniques have been developed. There are, for example, techniques described in U.S. Pat. No. 3,827,804, "Color Separation for Discrimination in Pattern Recognition Systems"; "The Classification of White Blood Cells", IEEE Transactions on Biomedical Engineering, Vol. BME-19, No.4, July 1972; and "Loukocyte Pattern Recognition", IEEE Transactions on Systems, Man and Cybernetics, Vol. CMC-2, No.4, July 1972. As described in the above publications, there is a system which recognizes white blood cells, especially the nuclei thereof, by discriminating a signal component of red blood cells from a sample of a whole blood by subtracting two signals from each other, each of which respectively corresponds to a green and a blue electric signal generated in response to respective green and blue light beams separated from a light beam which has passed through the sample of whole blood. This method utilizes the fact that the two signal components, as to the red blood cells included in the green and the blue light beams, are nearly equal to each other.

In order to classify the white blood cells automatically, however, it is necessary to determine the color of cytoplasm and the nucleus-cytoplasm ratio of the white blood cells, etc. It has been impossible to effect an automatic classification of white blood cells even from a detected image of the white blood cells due to the following. The sample of the whole blood is dyed with either one of a Wright Stain, A Giemza Stain, a Wright Glemza Stain and a May Giemza Stain. Due to the spectral absorbence of dyes in the sample of the whole blood the red blood cells appear reddish in the sample and the cytoplasm of the white blood cell appear light bluish and the nucleus of the white blood cell appear dark bluish. The absorption factor of the cytoplasms of the white blood cells, however, is generally lower than those of the nuclei thereof and of the red blood cells, and is nearly equal to that of the background in a bad part of the dye, and also depends upon the type of white blood cells even in a good part of the dye. Therefore, it is impossible to distinguish only the cytoplasms of the white blood cells with a fixed threshold level provided to discriminate the cytoplasms from others, so that information with respect to the cytoplasms thereof cannot be obtained by the above method.

SUMMARY OF THE INVENTION

An object of this invention is to provide a signal separation system applied to an automatic classification system for white blood cells.

Another object of this invention is to provide a signal separation system to discriminate a signal component as to cytoplasms of the white blood cells from a sample of whole blood.

Still another object of this invention is to provide a signal separation system to easily detect signal components of the nuclei of the white blood cells and red blood cells.

Another object of this invention is to provide a signal separation system which is capable of treating signal components for the sample of the whole blood with digital signals. depend In order to achieve these and other objects of this invention, a signal separation system, which comprises light separation means separating necessary light signal components from a light beam passed through the sample of the whole blood, means for forming a separation signal, and means for separating a signal component as to the cytoplasms of the white blood cells. The separation signal is generated through photoelectric converting means in accordance with received light signal components and binary signals are quantized with respect to certain threshold levels which depend on absorption characteristics relating to the sample of whole blood. The signal component to the cytoplasms is utilized by the automated classification system of white blood cells and facilitates a discrimination of white blood cells.

Other objects and advantages of this invention will be better understood by reference to the following detailed description when considered in connection with the accompanying drawings.

DESCRIPTION OF THE PREFERRED EMBODIMENTS

Figure 1:
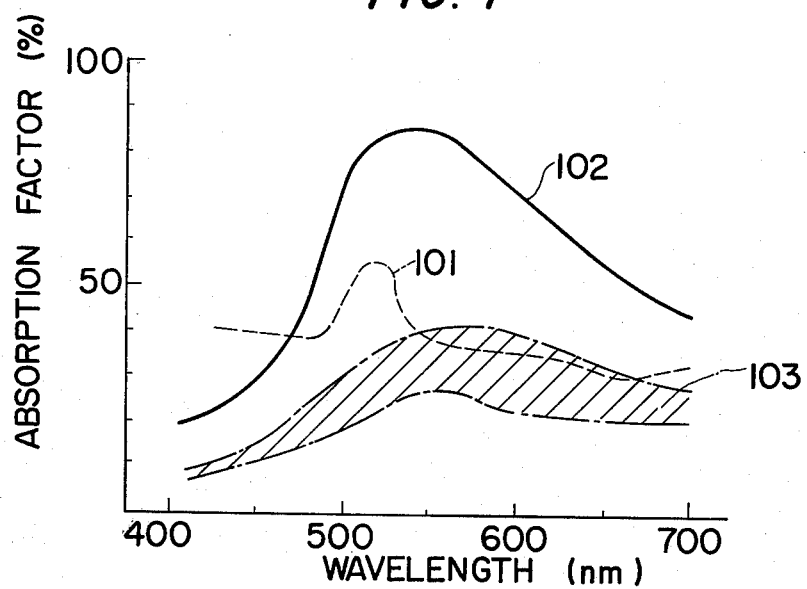
FIG. 1 is a graph of spectral absorption characteristics of a sample of whole blood.

Referring now to FIG. 1 which shows spectral absorption characteristics of a sample of whole blood, which is dyed with a Wright Stain, for example, a principle of this invention is based on the fact that an absorption factor (designated by numeral 101) of red blood cells is larger than absorption factors (designated by numerals 102 and 103) of the nuclei and cytoplasms of white blood cells in the blue region of the optical spectrum, the wavelength of which is in the range of 430 to 450 nm, and the absorption factor 102 of the nuclei of the white blood cells is larger than other absorption factors 101 and 103 in the green region of the optical spectrum, the wavelength of which is around 550 nm. Furthermore, although the region designated by the numeral 103 indicates an area in which the absorption factor of the cytoplasms of the white blood cells is dispersed in a good portion of dye, the absorption factor thereof in this area is larger than that of the background in the green region.

As will be understood from the above description, in the green region, the signal component of the nuclei of the white blood cells can be separated from the signal components of the cytoplasms thereof and the red blood cells by providing a certain threshold level. In the blue region, the signal component of the red blood cells can be separated from the signal components of the nuclei and the cytoplasms of the white blood cells by providing a certain threshold level. Both signal components of the nuclei of the white blood cells and the red blood cells are subtracted from a signal including the signal component of the cytoplasms of the white blood cells, so that the signal components of the cytoplasms and the background are obtained. The signal components after subtraction are separated into a signal component of the cytoplasms which exceeds the threshold level and to a signal component of the background which does not exceed it, so that only the signal component of the cytoplasms is obtained. This will be explained in greater detail with reference to FIGS. 2a–6.

Figure 2B:
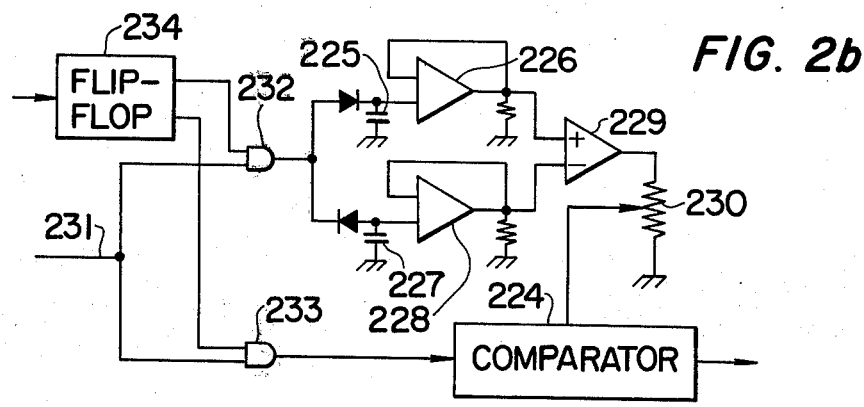
FIGS. 2b and 3b are concrete block diagrams of the parts of the signal separation systems shown in FIGS. 2a and 3a, respectively.
Figure 2A:
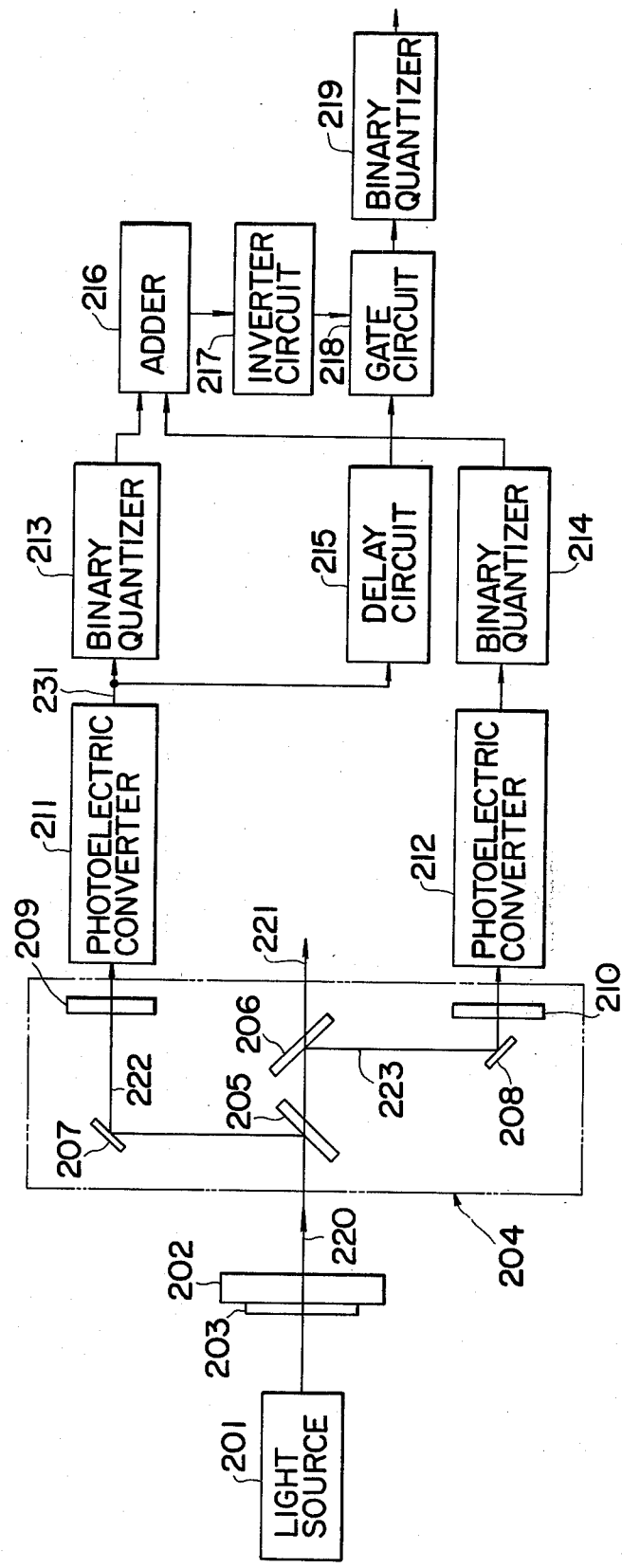

Referring to FIGS. 2a and 2b, a signal separation system includes a light source 201, a microscopic lens system (not indicated), a platform 202 for supporting a glass slide 203 containing a sample of whole blood, a light separator 204 comprising dichroic mirrors 205 and 206, mirrors 207 and 208, and filters 209 and 210, photoelectric converters 211 and 212, such as scanning type image pick-up tubes, binary quantizers 213, 214 and 219, a delay circuit 215, an adder 216, an inverter circuit 217 and a gate circuit 218. Each of the photoelectric converters may be a photomultiplier tube when the light source 201 is a flying spot scanner. The light source 201 generates a light beam 220 which passes through the glass slide 203. The light beam 220, after having passed through the sample, includes information as to the sample of whole blood. The light beam 220 is separated into three light components indicated by lines 221, 222 and 223 by conventional dichroic mirrors 205 and 206 placed at angles relative to each other, corresponding to respective red, green and blue light beams. Description as to the red light beam 221 will be omitted since it does not relate directly to this invention. The green light beam 222 includes the higher level signal component of the nuclei of the white blood cells than those of the cytoplasms thereof and the red blood cells as shown in the spectral absorption characteristics of FIG. 1; the blue light beam 223 includes the higher level signal component of the red blood cells than those of the nuclei and the cytoplasms of the white blood cells. The green light beam 222 passes through the filter 209, such as an interference filter and is received by the photo electric converter 211 converting the green light beam 222 to an electric signal. The filter 209 need not be used if the green light beam is sufficiently separated from the light 220. The output of the photoelectric converter 211 is applied to the binary quantizer 213 by which the signal components of the nuclei of the white blood cells and the others are converted to the binary signals "1" and "0", respectively.

The binary quantizer 213, hereinafter, will be described in more detail with reference to FIG. 2b. The binary quantizer 213 comprises means for providing a threshold level and a comparator 224, the output of which is controlled by the threshold level. The means for providing a threshold level comprises means for detecting and holding a maximum value of the signal from the photoelectric converter 211, which includes a capacitor 225 and an amplifier 226, means for detecting and holding a minimum value of the signal therefrom, which includes a capacitor 227 and an amplifier 228, means for detecting the voltage value of the subtraction, that is, the difference between the maximum and the minimum values of the signal therefrom, such as a subtractor 229, and a potentiometer 230 for providing a prescribed threshold level which is between the maximum and the minimum values. This prescribed threshold level of the potentiometer can be selected experimentally considering the characteristics of the light source, the light separator, the photoelectric converter, etc., the value of which is a level of about 50 to 60% with respect to the above difference. In the embodiment shown in FIG. 2a the threshold level is of about 55% of the difference. A control line 231 applies the electric signal from the photoelectric converter 211 to analog switches 232 and 233. A flip-flop circuit 234 receives pulse signals of one frame such as blocking signals of the scanning type image pick-up tube, the outputs of which control the analog switches 232 and 233, whereby electric signals from the photoelectric converter 211 are alternatively applied to the comparator 224 and to the means for providing the threshold level. As a result, the signal component of the nuclei and the other signal components are converted into binary signals 1 and 0, which are applied to the adder 216.

The blue light beam 223 passes through the filter 210, such as an interference filter and is received by the photoelectric converter 212 converting the blue light beam 223 into an electric signal. The filter 210 has such a characteristic that the center wavelength of the light passing therethrough is about 430 nm and the half-width thereof is about 15 nm, for example. The output of the photoelectric converter 212 is applied to the binary quantizer 214, the detailed construction of which is shown in FIG. 2b and in which maximum and minimum values of the output signals of the photoelectric converter 212 are detected and a threshold level is provided with a value corresponding to about 40 to 60 per cent, typically 50 per cent, with respect to the difference between the maximum and the minimum values thereof. As a result, the binary quantizer 214 produces the binary signals 1 and 0 with respect to the signal component of the red blood cells and the other signal components, respectively.

The outputs of the binary quantizer 213 and 214 are applied to the adder 216 in which a separation is provided to separate the signal components of the nuclei and the red blood cells from the signal representative of the sample of whole blood. The separation signal is applied to the gate circuit 218 through the inverter circuit 217 which operated to reverse the binary signals 1 and 0 from the adder 216 to the binary signals 0 and 1, in order to control the operation of the gate circuit 218 which may be a conventional analog switch. On the other hand, the output of the photoelectric converter 211 is applied to the gate circuit 218 through the delay circuit 215, the delay time of which is equal the time interval that the output signal of the photoelectric converter 211 is applied to the gate circuit 218 through the binary quantizer, the adder and the inverter circuit, so that the signal components of the cytoplasms of the white blood cells and the background are separated from the output signal of the photoelectric converter 211 and are applied to the binary quantizer 219, which may be constructed as shown in FIG. 2b. The binary quantizer 219 detects maximum and minimum values of the output signal of the gate circuit 218, the threshold level of which is set at a value corresponding to about 20 to 30 per cent, typically 30%, with respect to the difference between the maximum and the minimum values thereof, so that the signal component of the cytoplasms of the white blood cells is separated from that of the background and is obtained as the output of the binary quantizer 219.

Figure 3A:
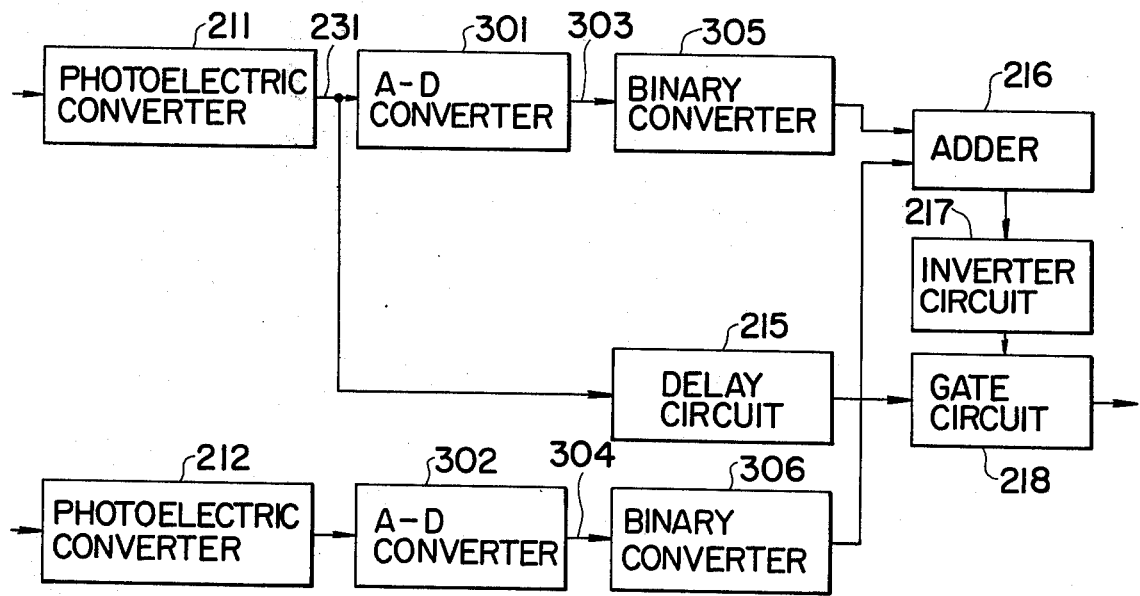
FIGS. 2a and 3a are schematic block diagrams of signal separation systems in embodiments of this invention.
Figure 3B:
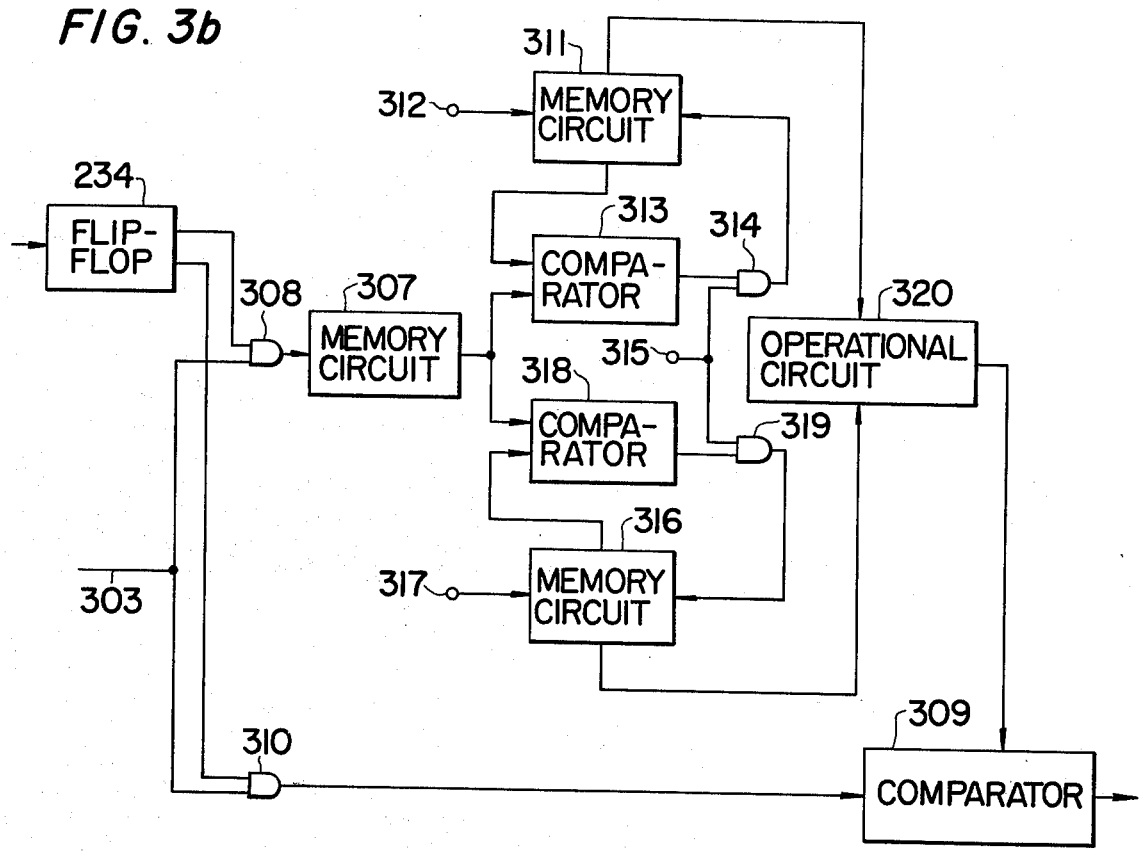

Referring now to FIGS. 3a and 3b, showing another embodiment of this invention, in which portions of the circuits shown in FIGS. 2a and 2b are omitted and the same elements shown in FIGS. 2a and 2b and FIGS. 3a and 3b are designated by the same reference numerals, the outputs of the photoelectric converters 211 and 212 are applied to A-D converters 301 and 302 so that the analog signals which are the outputs of the photoelectric converters 211 and 212 are converted to digital signals, respectively. The output digital signals 303 and 306, respectively, which are shown in FIG. 3b, in greater detail. The binary converter 305 comprises means for controlling the threshold level, including means for detecting and holding maximum and minimum levels of the output digital signal and an operational circuit 320, and a comparator 309. The digital output signal 303 is alternatively applied to a memory circuit 307 through a gate circuit 308 and to the comparator 309 through a gate circuit 310, controlled by the flip-flop circuit 234, as shown in FIG. 2b.

Now, the means for detecting and holding the maximum level will be described. The digital signals stored in the memory circuit 307 are compared in a comparator 313 with the level of the signal stored in memory circuit 311, the initial condition of which is set at a terminal 312, to which an earth potential is applied. The contents of the memory circuit 311 are rewritten when the signal level of the memory circuit 311 is lower than that of the memory circuit 307 and are maintained when the signal level of the memory circuit 311 is higher than that of the memory circuit 307.

With respect to the means for detecting and holding the minimum level, the digital signals of the memory circuit 307 are compared in a comparator 318 with the level of the signal stored in memory circuit 316, the initial condition of which is set at a terminal 317, to which a voltage source potential is applied. The contents of the memory circuit 316 are rewritten when the signal level of the memory circuit 316 is higher than that of the memory circuit 307 and are maintained when the signal level of the memory circuit 316 is lower than that of the memory circuit 307. The gate circuit 319 with the pulse input terminal 315 applies the result of the operation of comparator 318 to the memory circuit 316. The outputs of the memory circuits 311 and 316 corresponding to the maximum and the minimum values are applied to the operational circuit 320, in which the difference between the maximum and the minimum values is detected and a threshold level is provided with a value corresponding to about 50 to 60%, typically 55% with respect to the difference therebetween, as described in the previous embodiment. The threshold level, that is, the output signal of the operational circuit 320, is applied to the comparator 309 in order to convert the signal component of the nuclei of the white blood cells and the other signal components to the binary signals 1 and 0, respectively.

Although the binary converter 306 has the construction shown in FIG. 3b, the threshold level is provided with a value corresponding to about 40 to 60%, typically 50% with respect to the difference between the maximum and the minimum values of the output digital signal 304. The outputs of the binary converters 305 and 306 are applied to the adder 216. The operations of the other portions not being described here are as same as those shown in FIG. 2a.

Figure 4:
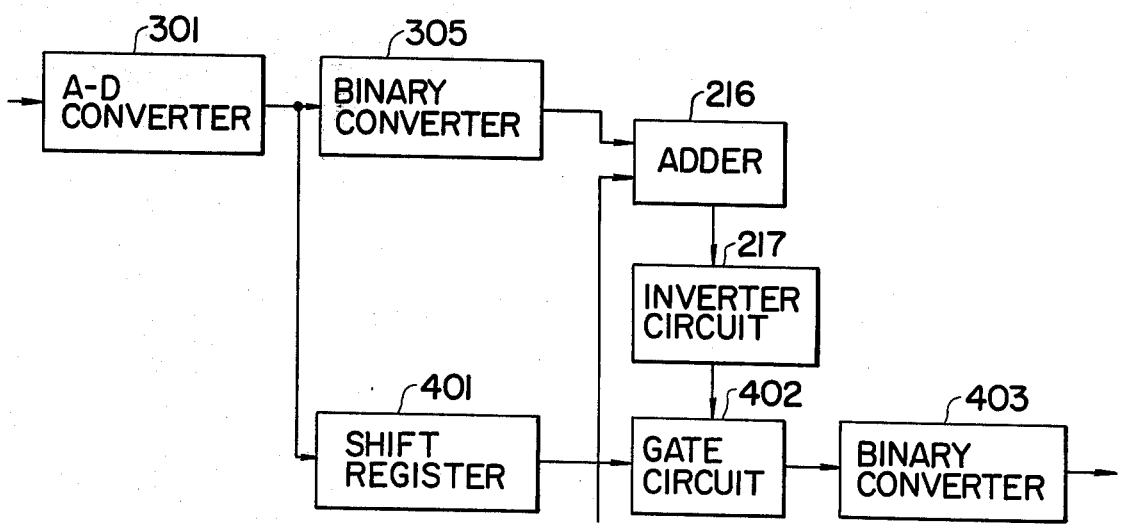
FIGS. 4 to 6 are schematic block diagrams of main parts of signal separation systems of embodiments of this invention.

The other embodiment of this invention, the main parts of which are shown in FIG. 4, provides a shift register 401 in place of the delay circuit 215, through which the output of the A-D converter 301 is applied to a gate circuit 402. In the gate circuit 402, the signal components of the cytoplasms of the white blood cells and the background are separated from the output signal of the shift register 401 and they are supplied to a binary converter 403. The delay time of the shift register 401 is equal to the time interval that the output signal of the A-D converter 301 is supplied to the gate circuit 402 through the binary converter 305, the adder 216 and the inverter 217. The advantages of the embodiment shown in FIG. 4 are that shift register 401, such as a counter, is able to be easily constructed by transistors, etc. rather than using the delay circuit 215 for the analog signals and the accuracy thereof is higher.

The binary converter 403 has the same construction shown in FIG. 3b, the threshold level of which is so selected that the signal components of the cytoplasms of the white blood cells and the background are separated from each other. The threshold level in this embodiment is provided with a value corresponding to about 20 to 35%, typically 30% with respect to the difference between a maximum and a minimum value of the output signal of the gate circuit 402.

Figure 5:
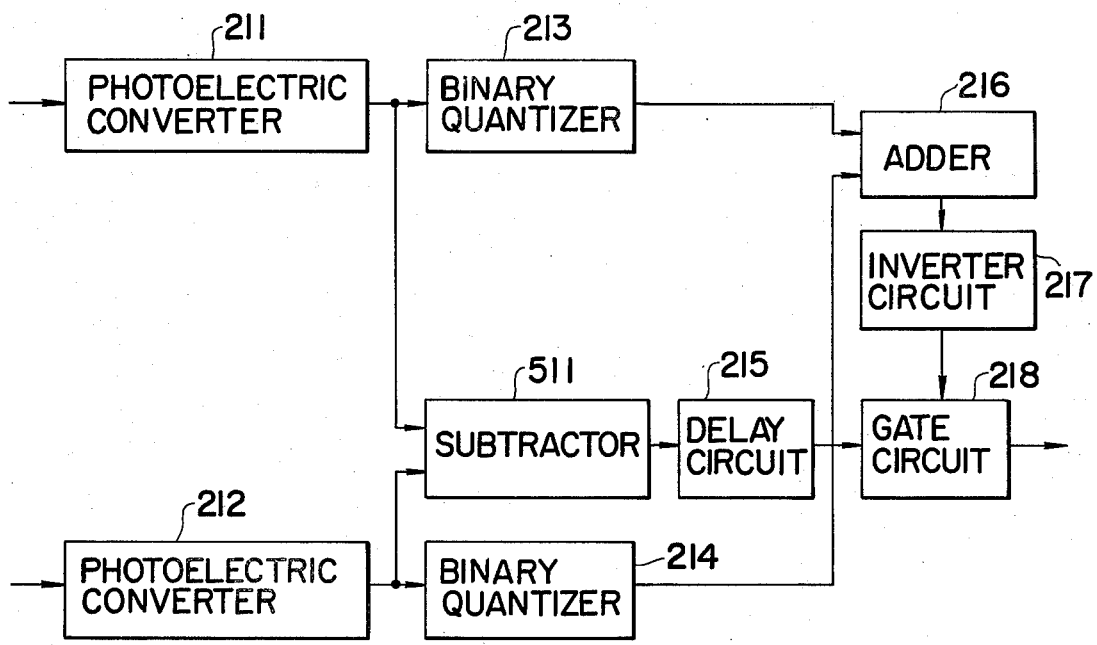
Figure 6:
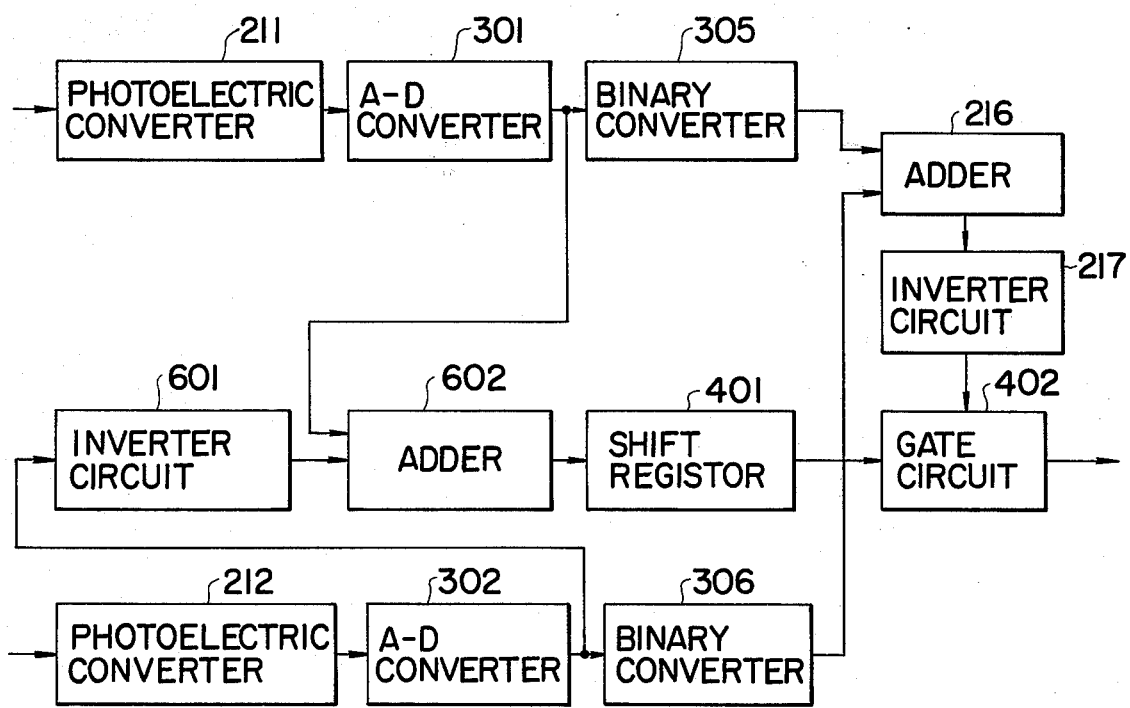

Referring now to FIGS. 5 and 6, other embodiments of the invention are shown. As is shown in FIG. 1, the levels of the absorption factors in the green and the blue regions with respect to the red blood cells are approximately equal. Therefore, a signal component corresponding to the subtraction of a blue signal component from a green signal component has a smaller absorption factor level with respect to the red blood cells so that it is easy to separate the signal component of the red blood cells. The embodiments shown in FIGS. 5 and 6 utilize the above principle.

In FIG. 5, the signal separation system in FIG. 2a further includes a subtractor 511, to which the outputs of the photoelectric converters 211 and 212 are applied. The delay circuit 215 receives the output of the subtractor 511, which eliminates the signal component of the red blood cells. It will be clearly understood that the delay time of the delay circuit 215 will be altered due to the subtractor 511.

In FIG. 6, the signal separation system is FIG. 4 further includes an inverter circuit 601 and an adder 602. The output of the A-D converter 301 is applied to the adder 602 and the output of the A-D converter 302 is applied to the adder 602 through the inverter 601. The shift register 401 received the digital output signal of the adder 602 which eliminates the signal component of the red blood cells.

Although the signal applied to the gate circuit utilizes either the green signal component or the subtracting signal between the green and the blue signal components in the above embodiments, either a signal corresponding to the light passed through the sample of the whole blood or a signal corresponding to the composite signal of the green, the blue and the red signal components after the light separator may be used.

While we have shown and described several embodiments in accordance with the present invention, it is understood that the same is not limited thereto but is susceptible of numerous changes and modifications as known to a person skilled in the art, and We, therefore, do not wish to be limited to the details shown and described herein but intend to cover all such changes and modifications as are obvious to one of ordinary skill in the art.

We claim:

1. A signal separation system comprising:
    first means for generating a beam of light and directing said beam of light through a sample of whole blood;
    second means, disposed in the path of the light beam which has passed through said sample of whole blood, for separating said light beam into first and second light beams, the magnitude of information representative of the nuclei of white blood cells in said sample being higher in said first light beam than in said second light beam, and the magnitude of information representative of red blood cells in said sample being higher in said second light beam than in said first light beam;
    third means, disposed to receive said first and second light beams, for generating first and second electric signals representative thereof;
    fourth means, receiving the first and second electric signals generated by said third means, for quantizing said first and second electric signals with respect to first and second prescribed threshold levels, and producing respective first and second binary signals representative of the quantized first and second electric signals;
    fifth means, coupled to said fourth means, for combining said first and second binary signals and producing a first separation signal which contains a signal component representative of the nuclei of white blood cells in said sample and a signal component representative of red blood cells in said sample; and
    sixth means, coupled to said fifth means, and said third means, and responsive to said first separation signal and the output of said third means, for producing a second separation signal representative of the cytoplasm in the white blood cells of said sample.

2. A signal separation system according to claim 1, wherein said first and second light beams have respectively different wavelengths.

3. A signal separation system according to claim 2, wherein the wavelength of said first light beam lies in the green region of the optical spectrum and the wavelength of said second light beam lies in the blue region of the optical spectrum.

4. A signal separation system according to claim 3, wherein said sixth means comprises
    a gate circuit, which is controlled by said first separation signal to gate said first electric signal therethrough, and
    a binary quantizing circuit which receives the output of said gate circuit and produces said second separation signal.

5. A signal separation system according to claim 4, wherein said fourth means comprises first and second binary quantizers which receive said first and second electric signals, respectively, and produce said first and second binary signals, and
    wherein said fifth means comprises an adder circuit which adds said first and second binary signals, from said first and second binary quantizers, to each other, and an inverter circuit connected to the output of said adder circuit.

6. A signal separation system according to claim 3, wherein said sixth means comprises
    a gate circuit, which is controlled by said first separation signal,
    a subtractor circuit, coupled to said third means, to subtract said first and second electric signals from each other,
    a delay circuit coupled between said subtractor circuit and said gate circuit, and
    a binary quantizing circuit which receives the output of said delay circuit, as gated by said gate circuit under the control of said first separation signal, and produces said second separation signal.

7. A signal separation system according to claim 4, wherein said sixth means further comprises a delay circuit coupled to said third means, for delaying said first electric signal therefrom and applying the delayed first electric signal to said gate circuit.

8. A signal separation system according to claim 4, wherein said fourth means comprises
    first and second analog-to-digital converters for converting said first and second electric signals into first and second digital signals, respectively, and
    first and second binary converters for converting said first and second digital signals into said first and second binary signals, respectively.

9. A signal separation system according to claim 8, wherein said sixth means further comprises a delay circuit coupled to said third means, for delaying said first electric signal therefrom and applying the delayed first electric signal to said gate circuit.

10. A signal separation system according to claim 8, wherein said sixth means further includes a shift register connected between the output of said first analog-to-digital converter and said gate circuit, said first digital signal being applied to said shift register.

11. A signal separation system according to claim 8, wherein said sixth means further includes
    an inverter circuit connected to the output of said second analog to digital converter,
    an adder, connected to the output of said inverter circuit and said first analog-to-digital converter, and
    a shift register connected between the output of said adder and said gate circuit.

12. A signal separation system according to claim 1, wherein said first means comprises a flying spot scanner, and said third means comprises first and second respective photomultiplier tubes.

13. A signal separation system according to claim 1, wherein said third means comprises first and second respective scanning type image pick-up tubes.

14. A signal separation system according to claim 5, wherein each of said first and second binary quantizers comprises a maximum level detector and hold circuit and a minimum level detector and hold circuit, coupled to receive a respective one of said first and second electric signals, a subtraction circuit connected to subtract the outputs of said maximum level detector and hold circuit and said minimum level detector and hold circuit from each other, and a threshold comparator circuit for comparing the level of a respective one of said first and second electric signals with a prescribed threshold level as determined by the output of said subtraction circuit.

15. A signal separation system according to claim 8, wherein each of said first and second binary converters respectively comprises a first memory circuit coupled to receive a respective one of said first and second digital signals, second and third memory circuits, the memory contents of which are initally presettable, first and second comparing circuits, coupled to the outputs of said second and third memory circuits, for comparing the contents of said second and third memory circuits with the contents of said first memory circuit and for causing the contents of said second and third memory circuits to be respectively rewritten only in response to the contents of said second and third memory circuits being respectively higher and lower than that of said first memory circuit, an operational circuit, connected to said second and third memory circuits, for detecting whether or not the difference between the contents of said second and third memory circuits exceeds a preselected threshold level, and a comparator circuit, for comparing the respective one of said first and second electrical signals with the output of said operational circuit, and converting the respective one of said first and second binary signals in accordance with said comparison.

* * * * *